(12) United States Patent
Green

(10) Patent No.: US 10,705,066 B2
(45) Date of Patent: Jul. 7, 2020

(54) METHOD AND SYSTEM FOR SPECTRAL DETERMINATION OF EGG GENDER AND FERTILITY

(71) Applicant: Zen Genetics Ltd., Tel-Aviv (IL)

(72) Inventor: Yehoshua Green, Tel-Aviv (IL)

(73) Assignee: Zen Genetics Ltd., Tel-Aviv (IL)

( * ) Notice: Subject to any disclaimer, the term of this patent is extended or adjusted under 35 U.S.C. 154(b) by 0 days.

(21) Appl. No.: 16/623,789

(22) PCT Filed: Jun. 12, 2018

(86) PCT No.: PCT/IL2018/050646
§ 371 (c)(1),
(2) Date: Dec. 18, 2019

(87) PCT Pub. No.: WO2018/235070
PCT Pub. Date: Dec. 27, 2018

(65) Prior Publication Data
US 2020/0110068 A1    Apr. 9, 2020

Related U.S. Application Data

(60) Provisional application No. 62/521,453, filed on Jun. 18, 2017.

(51) Int. Cl.
G01N 21/00 (2006.01)
G01N 33/08 (2006.01)
G01N 21/25 (2006.01)
G01N 21/31 (2006.01)

(52) U.S. Cl.
CPC ......... *G01N 33/085* (2013.01); *G01N 21/255* (2013.01); *G01N 21/31* (2013.01)

(58) Field of Classification Search
CPC ... H01J 37/32935; G01N 21/64; G01N 21/68; G01N 2015/1037; G01J 3/02
USPC .......................................................... 356/72
See application file for complete search history.

(56) References Cited

U.S. PATENT DOCUMENTS

| | | | |
|---|---|---|---|
| 2005/0206876 A1* | 9/2005 | Reeves | A01K 43/00 356/52 |
| 2009/0201323 A1 | 8/2009 | Robert et al. | |
| 2014/0327902 A1 | 11/2014 | Giger et al. | |

FOREIGN PATENT DOCUMENTS

| | | |
|---|---|---|
| WO | WO 2014/086335 | 6/2014 |
| WO | WO 2015/145435 | 10/2015 |
| WO | WO 2018/235070 | 12/2018 |

* cited by examiner

*Primary Examiner* — Md M Rahman

(57) ABSTRACT

A method for detecting a state of an egg, the method comprising: illuminating an egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; capturing a reflection of at least a portion of the plurality of light pulses at a time delay corresponding to light reflected from within said egg in an interval of between about 1 mm and about 20 mm; analyzing the captured reflection to determine at least one spectrum of each of said plurality of light pulses; and classifying at least one of a gender and a fertility state of said egg according to said at least one spectrum.

20 Claims, 5 Drawing Sheets

METHOD AND SYSTEM FOR SPECTRAL DETERMINATION OF EGG GENDER AND FERTILITY

RELATED APPLICATIONS

This application is a National Phase of PCT Patent Application No. PCT/IL2018/050646 having International filing date of Jun. 12, 2018, which claims the benefit of priority under 35 USC § 119(e) of U.S. Provisional Patent Application No. 62/521,453 filed on Jun. 18, 2017. The contents of the above applications are all incorporated by reference as if fully set forth herein in their entirety.

FIELD AND BACKGROUND OF THE INVENTION

The present invention, in some embodiments thereof, relates to spectral methods and systems, more particularly, but not exclusively, to time-resolved spectral methods and systems for determining an egg condition.

Each year billions of eggs are produced in the United States. Duration of incubation for chicken eggs hatching takes about 21 days and consumes time and energy. At least 50% of fertilized eggs contain male chicks, which are useless to a hatchery that is dedicated to raising egg-laying hens. The determination of the sex of the chick is typically not performed until the chick is hatched, at which point, male chicks are disposed of. In addition, a significant percentage, typically 10 to 40%, of eggs is infertile. These useless eggs consume space and energy within an incubator, and can also cause contamination of other eggs. In addition to the energy costs of incubating a useless egg to maturity, there is the problem of eliminating the male chicks after hatching. In such an industry, efficient quality control and limiting production costs are required. To this end, a number of non-invasive techniques have been developed for assessing the condition of unhatched eggs.

Time-resolved spectral imaging, which acquires spectral information at a desired time scale, may be used for detecting various agricultural products.

SUMMARY OF THE INVENTION

According to an aspect of some embodiments of the present invention there is provided a method for detecting a state of an egg. According to some embodiments, the method comprising: illuminating an egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; capturing a reflection of at least a portion of the plurality of light pulses at a time delay corresponding to light reflected from within said egg in an interval of between about 1 mm and about 20 mm; analyzing the captured reflection to determine at least one spectrum of each of said plurality of light pulses; and classifying at least one of a gender and a fertility state of said egg according to said at least one spectrum.

According to an aspect of some embodiments of the present invention there is provided a method for detecting a state of an egg. According to some embodiments, the method comprising: illuminating an egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; capturing a reflection of at least a portion of the plurality of light pulses at a temporal resolution of between about 0.5 ps and about 500 ps; analyzing the captured reflection to determine at least one spectrum of each of said plurality of light pulses; and classifying at least one of a gender and a fertility state of said egg according to said at least one spectrum.

According to some embodiments of the invention the method, wherein each of at least some of said plurality of light pulses has an intensity of between about 0.2 and about 10 mJ per pulse.

According to some embodiments of the invention, the method further comprising configuring each of at least some of said plurality of light pulses to comprise light at a first wavelength of between about 300 nm and about 750 nm and light at second wavelength of between about 900 nm and about 1400 nm.

According to some embodiments of the invention the method, wherein the first wavelength is between about 500 nm and about 700 nm and the second wavelength is between about 950 nm and about 1350 nm.

According to some embodiments of the invention the method, wherein each of at least some of the plurality of light pulses having a beam area of between about 0.5 and about 5 $mm^2$.

According to some embodiments of the invention the method, wherein the capturing a reflection of plurality of light pulses is by directing the reflected light pulses into a streak camera.

According to some embodiments of the invention, the method further comprises discarding the egg for which said condition does not match a predetermined condition.

According to some embodiments of the invention the method, wherein said classifying is carried out up to 7 days after incubation of the egg.

According to some embodiments of the invention the method, wherein said classifying is carried out up to 3 days after incubation of the egg.

According to some embodiments of the invention the method, wherein said classifying is carried out up to 1 day after incubation of the egg.

According to some embodiments of the invention the method, wherein said at least one spectrum is selected from a group consisting of: a reflectance spectrum, a transmittance spectrum, a fluorescence spectrum and a derivative spectrum.

According to some embodiments of the invention the method, wherein said at least one of the spectrum is obtained by analyzing a portion of captured light emanated from said egg at an angle below about 180° relative to a longitudinal axis of the egg.

According to some embodiments of the invention the method, wherein said time delay is set from time of illuminating said egg with a plurality of light pulses.

According to an aspect of some embodiments of the present invention there is provided a system for detecting a condition of an egg. According to some embodiments, the system comprising: a light source for illuminating the egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; a detector for capturing a reflection of at least a portion of the plurality of light pulses at a time delay corresponding to light reflected from within said egg in an interval of between about 1 mm and about 20 mm; a processor for analyzing the captured reflection to determine at least one spectrum of each of said plurality of light pulses so as to classify at least one of a gender and a fertility state of said egg according to said at least one spectrum.

According to an aspect of some embodiments of the present invention there is provided a system for detecting a condition of an egg. According to some embodiments, the system comprising: light source for illuminating the egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; a detector for capturing a reflection of at least a portion of the plurality of light pulses at a temporal resolution of between about 0.5 ps and about 500 ps; a processor for analyzing the captured reflection to determine at least one spectrum of each of said plurality of light pulses so as to classify at least one of a gender and a fertility state of said egg according to said at least one spectrum.

According to some embodiments of the invention, the system as delineated herein, wherein the detector comprises a streak camera.

According to some embodiments of the invention, the system as delineated herein, wherein the detector having a resolution between about 1 ps and about 300 ps.

According to some embodiments of the invention, the system as delineated herein, wherein the light source comprises at least one laser.

According to some embodiments of the invention, the system as delineated herein, wherein the laser is a diode pumped laser.

According to some embodiments of the invention, the system as delineated herein, wherein the laser is a Nd:YAG laser.

According to some embodiments of the invention, the system as delineated herein, wherein the laser is a wavelength tuneable laser.

According to some embodiments of the invention, the system as delineated herein, comprising a trigger jitter having a resolution below 200 ps.

Unless otherwise defined, all technical and/or scientific terms used herein have the same meaning as commonly understood by one of ordinary skill in the art of time-resolved spectroscopic imaging and in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
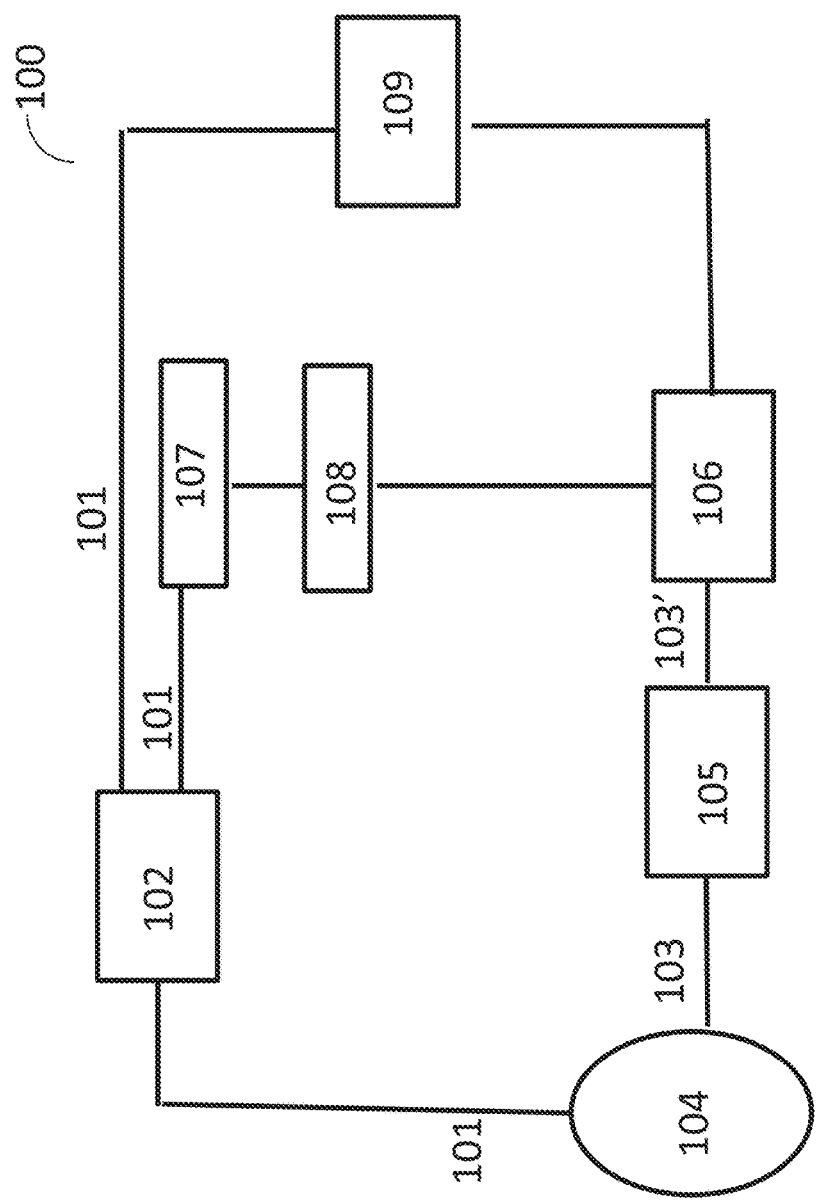
FIG. 1 is a schematic illustration of a system for spectral analysis of an egg according to some embodiments of the present invention.

The present invention, in some embodiments thereof, relates to spectral methods and systems, more particularly, but not exclusively, to spectral methods and systems for determining an egg condition.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As used herein, the term captured spectrum (e.g., reflectance, and/or transmittance, and/or absorbance, and/or fluorescence, and/or derivative) refers to a measurement in which a plurality of electromagnetic radiations impinges on a target egg, and the intensity of the electromagnetic radiation as a function of its wavelength coming from a specific media in said egg is recorded to acquire data subsequent to an interaction of the electromagnetic radiation with said specific media and/or a mathematical manipulation applied on the acquired data. At least a portion of each of the electromagnetic radiations is captured, and at least one spectrum of each of said plurality of electromagnetic radiations is determined by analyzing a portion of the captured electromagnetic radiation, preferably electromagnetic radiation reflected from the target egg. The plurality of electromagnetic radiations may alternatively or additionally comprise radiation transmitted-through and/or absorbed-by the specific media in the target egg, as will be further described below.

Reflectance spectrum specifically refers to a spectrum in which intensity of a plurality of electromagnetic radiations emitted and/or reflected from a target is measured at any angle relative to incident light. In some embodiments, the reflectance spectrum specifically refers to a spectrum in which a detector is placed in such a manner as to measure intensity of electromagnetic radiation emitted and/or reflected from a target at any angle relative to incident light.

Transmission spectrum specifically refers to a spectrum in which intensity of a plurality of electromagnetic radiations passing through a target at an angle of about 180° relative to incident light is measured. In some embodiments, the transmission spectrum specifically refers to a spectrum in which a detector is placed in such a manner as to measure intensity of electromagnetic radiation that passes through a target at an angle of about 180° relative to incident light.

Fluorescence spectrum specifically refers to a spectrum in which intensity of a plurality of electromagnetic radiations returned and/or emitted from the target at a wavelength longer than a wavelength of impinging light is measured.

Inspection angle refers to an angle between a light beam and capturing means, e.g., a detector, which may vary during a spectral measurement in order to obtain spectral information in accordance with the present invention.

As appreciated, reflectance, and/or transmission, and/or absorption and/or fluorescence modes are not pure modes, as they are affected by scattering and reflection degrees. Reflection is affected by the transmittance degree, which in turn, is affected by scattering and reflection degrees. As further appreciated, the egg system is complex and at times may not be simply characterized in terms of pure reflectance (and/or transmittance and/or absorbance), as light is inspected from the volume of the egg and not only from the egg's surface. In addition, reflected light travelling to the detector is also only partially absorbed.

Captured light (and/or transmitted light, and/or absorbed light) is obtained by measuring the amount of radiation reflected by (and/or transmitted-through and/or absorbed-by, respectively) specifically a germinal disk within an egg target at a plurality of predetermined wavelengths. Germinal disk refers to an organ within an egg, specifically, a distinct small circular spot on a surface of a yellow egg yolk containing information of fertility and/or gender of an egg.

As appreciated, the reflected electromagnetic radiation is affected by, inter alia, absorbance.

Spectral information may be obtained according to the invention by using a spectrum selected from reflectance, and/or transmission, and/or absorbance, and/or fluorescence and/or derivative and/or any combination thereof. In some embodiments, spectral information is obtained by spectra comprising a combination of reflectance and fluorescence.

The plurality of predetermined wavelengths may comprise a first set of spectral range which may provide information on fertility of an egg, e.g., spectral range of between about 200 nanometer (nm) and 1000 nm, preferably, between about 200 nm and 550 nm, between about 650 nm and 1000 nm, or more preferably between about 550 nm and about 650 nm. A second set of spectral range which may provide information on gender of an egg may be between about 1000 nm and about 1400 nm, more preferably between about 1200 nm and about 1300 nm.

Spectral range of about 500 nm may be used for detecting the fertility, whereas spectral range of about 1300 nm may be used for determining the gender. This range includes vibrational overtones that are related to the differences in the vibrational spectra of the germinal disk of male and female eggs.

As appreciated, quality and accuracy of detection of spectral information of an egg using time-resolved spectral analysis is influenced by various parameters such as egg shell color (white and/or brown egg), time after an egg has been settled in an incubator, egg size and shape, egg morphology, type of spectroscopic method (optical, reflectance, transmittance), signal-to-noise ratio (SNR), statistical analysis method, light source, design of spectrometer system, time required to obtain an image from spectroscopic measurement, time required to measure egg fertility after an egg has been settled in an incubator, etc.

Typical methods and systems for predicting spectral information, such as egg gender and/or egg fertility, are insensitive and unreliable, in particular, during early stages of incubation after the egg has been settled in an incubator.

One of the problems in spectral analysis of eggs for identification of egg gender and/or fertility is that most of the light is absorbed and/or reflected from the egg's outer shell, inner shell and other egg organelles that do not contain relevant spectral information with respect to gender and fertility. Although light reaching the detector may contain information on egg's gender and fertility, the relevant signals are mixed in more intense signals from the other egg's organelles. Extracting only relevant information with respect to egg's gender and fertility from the egg's organelles, specifically, from the egg's germinal disk, is not possible, especially, at early stages of incubation, in which the intensity of the signal of the egg's gender and fertility is weak. Light related to organelles other than germinal disk is much stronger and influenced by various effects, such as color of the shell, etc.

Some typical spectral methods for detecting the condition of an avian egg utilize a neural network algorithm to compare the spectrum of a test egg against a spectral library, however, such method can detect the avian egg gender only from about the 12th day after laying.

Thus, a non-invasive method and system for detecting a state of an egg, e.g., egg gender and egg fertility, at very early stages after an egg has been settled in an incubator, is highly desired.

The inventor has found that by utilizing a system designed and operative as described herein, accurate detection of egg fertility and/or egg gender (and/or other properties indicating condition of an egg) may be obtained, specifically, during very early stages of incubation, e.g., within 7 days that an egg is settled in an incubator, preferably 3 days, more preferably 1-2 days after an egg is settled in an incubator.

The system according to the invention utilizes a light source that is operative at a pulse width providing temporal resolution in picoseconds scale, e.g., below about 500 ps, and that has a predetermined intensity and wavelength range. Such system is efficient in determining inter-egg spectral information of egg fertility and/or egg gender, specifically obtained from an egg's germinal disk, during early stages of incubation.

Inter-egg spectral information may be obtained, according to the present invention, by irradiating a target egg by short time-resolved pulses of light, which pass through the egg's organelles and arrive at the germinal disk within an egg to be detected. Spatial resolution according to the present invention refers to ability to obtain information needed to assess fertility and/or gender of the egg with a sufficiently high SNR. Light may be reflected by, and/or absorbed by, and/or transmitted through at least one of the organelles and captured by a detector having picoseconds temporal resolution, preferably below 500 picoseconds, more preferably between about 0.5 picoseconds and about 500 picoseconds. The captured light may provide desired spectral information corresponding to fertility and/or gender of the target egg.

Some of the light from a desired inter-egg media may reach a detector having picoseconds time resolution and configured to capture and measure a spectrum related to the desired inter-egg spectral information. The propagation of light in the desired inter-egg media results in spatial resolution of less than 20 mm in the egg, preferably, less than 10 mm, more preferably, less than 5 mm. The light is captured in a time delay, which corresponds to light traveling from the light source to penetrate a target egg and then reaching a predetermined inter-egg location, and then reflected from (and/or absorbed in, and/or passing through) said location towards the detector at an interval of less than 20 mm, preferably between 1 mm and 20 mm.

The inventor has found that when utilizing the method of the invention at predetermined wavelengths described herein, maximum transparency of egg shell is provided, therefore accurate spectral analysis for obtaining desired information of the state of fertility and gender of an egg may be obtainable. Such advantageous wavelength range, may be from UV region to NIR region of spectrum; such as from between about 200 nm and about 400 nm (in UV region), to between about 700 nm and about 2000 nm (in NIR region). In some preferred embodiments, the predetermined wavelength range is from UV region of between about 200 nm and about 370 nm, between about 450 nm and 550 nm, and to NIR region of between about 1000 nm and about 1500 nm.

Transparence of an egg may increase at between about 450 nm and about 550 nm, and between about 1000 nm and 1500 nm.

The information needed to assess the fertility and/or gender of an egg with a sufficiently high signal-to-noise ratio (SNR), may be achieved by collecting the signals coming from the germinal disk and omitting those coming from the shell and other egg's organelles. The desired spatial resolution is achieved using short (picoseconds) laser pulses and a gated detector operative in time resolution in picosecond range.

Thus, the invention provides a system and method for measurement of restricted light originating only from a germinal disk and its surroundings, where compounds relating to the egg's organelles, which determine the gender and the fertility of the target egg, are located.

The system and method according to the present invention is advantageous as the light captured by the detector arrives essentially from a location in the egg where the relevant materials to be detected are located (i.e., germinal disk), and not from other organelles that contain irrelevant spectral information. Specifically, light from the egg's shell having a high intensity is differentiated from the light having lower intensity derived from the germinal disk, such that the intensity of the irrelevant materials do not interfere with the desired intensity from the germinal disk.

To enable high spatial resolution within an egg, the present invention utilizes a detector, e.g., a short-pulse gated detector (time-gated), that may be set to respond to light that arrives only at a predetermined time delay after the initial light pulse is illuminated from the light source to provide a gated image. Time delay is set such that it corresponds to light arriving solely from the germinal disk. Provided the speed of light (ca. $3 \times 10^8$ m/s in vacuum), a temporal delay may be attributed to a certain photon trajectory that comes from the germinal disk, such that temporal resolution in the detector is transformed into spatial resolution within the egg of between about 1 mm and about 20 mm.

Thus, according to some of its aspects, the present invention provides a method for detecting a state of an egg, the method comprising: illuminating an egg with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; capturing light reflected from, and/or absorbed in, and/or passing through the target egg. The light is captured in a time delay, which corresponds to light traveling from the light source to penetrate a target egg, and reaching a predetermined location inside the target egg, and then reflected from (and/or absorbed in, and/or passing through) said location towards the detector, at an interval of between 1 mm and 20 mm, which provides desired spectral information corresponding to fertility and/or gender state of the target egg.

The method according to the present invention further comprises analyzing the captured reflection to determine at least one spectrum of each of said plurality of light pulses; and classifying at least one of a gender and a fertility state of said egg according to said at least one spectrum.

Figure 2:
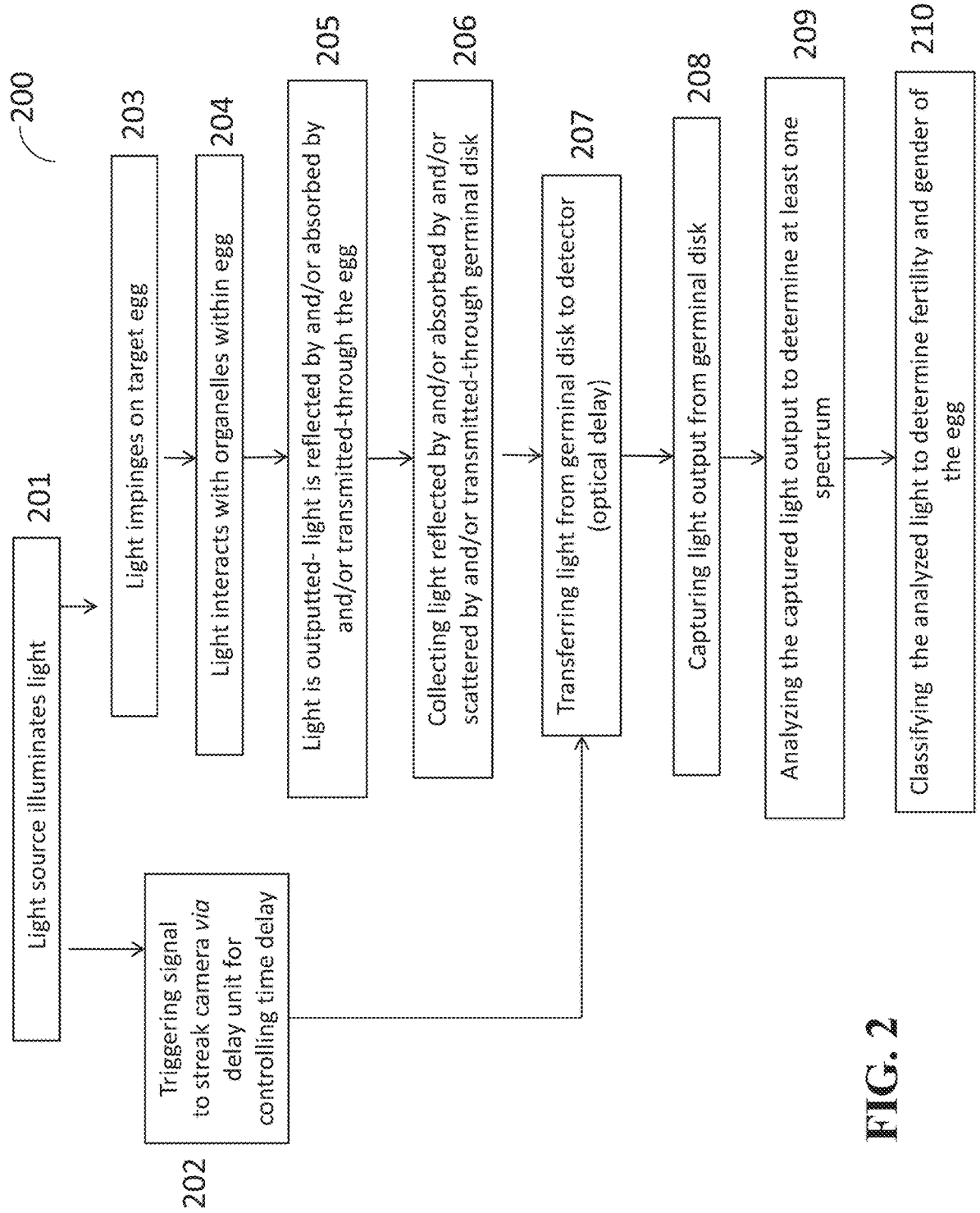
FIG. 2 is a flow chart illustrating a method for spectral analysis of an egg according to some embodiments of the present invention.

Reference is now made to FIG. 1, which presents a schematic illustration of system 100 for spectral analysis of an egg, according to some embodiments of the present invention. Reference is also made to FIG. 2, which presents a flow chart of the method 200 for detecting a state of an egg, according to some embodiments of the present invention.

System 100 provides light source 102 for illuminating light 201 over a desired wavelength range. Light beam is illuminated 101 from the light source 102 and impinges 203 on a target egg 104. Light source 102, may preferably be and/or comprise a laser light source, more preferably, may be and/or comprise a picosecond laser. In some embodiments, the laser may comprise a laser selected from a diode pumped laser, an OPO laser and a Nd:YAG laser, such as a diode pumped picosecond YAG laser. Alternatively, the laser is a flash-lamp pumped pulsed Nd:YAG laser, preferably of 1064 nm. In some exemplary embodiments, light source 102 may be equipped with harmonic generators and with OPO (Optical Parametric Oscillator) laser that allows its wavelength tuning in the UV-IR-NIR ranges, or a part of these ranges. Such setup allows for tuning the laser radiation from UV to IR range.

The light pulses impinging on the target egg 203 may be focused on a predetermined region of the egg, to provide light that interacts with organelles 204 in a media in said egg for obtaining spectral information (fertility and gender), e.g., from the germinal disk.

Absorbance of electromagnetic radiation depends, inter alia, on the absorbance of material, which is wavelength dependent. The material composition in germinal disk, changes after fertilization, which results in modified optical absorbance and reflectance. Differences between genders may be manifested in accordance with some embodiments of the present invention, which may be due to differences between DNA compositions of each gender. Interactions 204 between electromagnetic radiation and materials in the germinal disk are electronic excitations in the UV-Vis range and vibrational/rotational excitations in the IR-NIR range, including overtones.

Light from the germinal disk, e.g., from reflections, may be enhanced by, e.g., rotating the target egg 104 and/or the light source 102 such that the germinal disk is in close proximity to the rotation axis. As such, other signals coming from distances different than the signal related to the germinal disk may be decreased.

In some embodiments, the light source 102 may comprise a tunable light source 102, which may be controllable by a controller coupled to a computer 110 to provide light in a set of wavelengths and/or intensities that may be focused on a target egg 104 to interact 204 with a region in an egg media that provides desired inter-egg spectral information (fertility and gender). Controller may be chosen such that each impinging light pulse on said egg 203 comprises light at tunable wavelengths for interactions between electromagnetic radiation and organelles 204 in the germinal disk. e.g., electronic excitations in the UV-Vis range and vibrational/rotational excitations in the IR-NIR range, including overtones.

Controller may be an electronic control apparatus of any type known in the art such that the light from the light source 102 is tunable, namely, light intensity provided by the light source 102 from pulse to pulse, may vary less than a predetermined amount from a normative intensity at a predetermined pulse width. Preferably, the controller controls the light intensity so that the pulse to pulse intensity variance is less than a predetermined percentage, e.g., less than 10%, of the normative intensity. The normative intensity for about 3 ps pulse width may correspond to up to about 2 Joule per $cm^2$ ($J/cm^2$) radiation energy intensity of a pulse of laser light imaged by lens on the target egg.

In some embodiments, the plurality of pulses of light may each be illuminated at a plurality of wavelengths spaced between every about 0.01 nm and about 1 nm in a range of wavelengths between about 400 nm and about 1500 nm. In some embodiments of the invention, the number of the plurality of pulses is between 10 and 500 and/or $10^3$ to $10^7$ (depending on laser type).

Light source 102 may illuminate light pulses at a light intensity between about 0.1 milliJoule (mJ) and about 100 mJ per pulse, preferably between about 0.2 mJ and about 10 mJ per pulse, more preferably, between about 0.8 mJ and 2 mJ per pulse. The beam diameter of the light pulses impinging on the egg shell may be between about 0.5 and 15 $mm^2$, preferably, between about 0.8 and about 3 $mm^2$.

In various exemplary embodiments of the system 100, light source 102 may operate at a pulse width in the picoseconds scale, e.g., less than about 500 picoseconds, preferably between about 1 picoseconds (ps) and about 500 ps, or preferably between about 1 ps and about 300 ps, or preferably between about 1 ps and about 200 ps, or preferably between about 1 ps and about 100 ps, or preferably between about 10 ps and about 200 ps, or preferably between about 10 ps and about 100 ps, or more preferably between about 20 ps and about 100 ps.

The inspection angle between the light beam and the detector may vary during a spectral measurement in order to obtain tomographic information. As shown in FIG. 1, the inspection angle is 90° in reflectance mode, alternatively, the inspection angle may be 180° in transmission mode. In some preferred embodiments of the invention, the spectrum is measured in reflectance mode, in which a detector is placed at any angle lower than 180° relative to the incident light.

The detector according to the present invention may comprise at least one of the components: collecting optics 105, streak camera 106, trigger 107, delay unit 108, power supply and a controller. Light outputted 103, 205 from the germinal disk in said egg 104 and optionally its surroundings, e.g., reflected light (and/or absorbed light, and/or transmitted light and/or scattered light), may be collected via collecting optics 105, 206 and transferred to an input 207 of a streak camera 106 of a detector, preferably a picosecond gated light detector, configured to capture light from the germinal disk 208 over a time window 209 set by the streak camera 106, which transfers light from spectral region relating to the germinal disk 207 to the detector. The intensity of the reflected light (and/or absorbed light, and/or transmitted light) depends on the inspection angle.

Collecting optics 105 may comprise a lens system for focusing the outputted light, and/or optical fibers. The size of the time window determines the time interval selected and displayed at the detector. In some embodiments, multiple measurements are made of a plurality of eggs, and each egg is then averaged in order to increase the SNR. In some embodiments, multiple measurements are made of each egg at various inspection angles in order to obtain information for tomographic analysis.

In order to design the streak camera to perform the capturing of the light from the germinal disk in the time window as above said, a delay unit may be included. The delay unit 108 may comprise an optical setup through which light may be transferred such that light arrives at the detector input in a delay corresponding to the time window 207, e.g., through a mirror and/or a set of mirrors or through an optical fiber, such that said light arrives at the streak camera 106 of a detector at a delay. The delay may be determined by the additional path or by the fiber's length, such that light reflected from the egg's shell falls out of the streak camera's 106 measurement window and light originating from the germinal disk falls inside the streak camera's 106 measurement window.

In order to control the time delay for generating operation of measurement by the streak camera 106, a pulse of light 101 from light source 102 may be transmitted to trigger 107, which functions to trigger a signal 202 to the delay unit 108 at a time window corresponding to light arriving from the germinal disk. The time window may be programmable and controlled by a computer 109 and/or electronic components, preferably included within the light source 102. The trigger signal may be fed into a streak camera 106. In some embodiments, the trigger 107 comprises a trigger jitter having a resolution below 500 ps, preferably below 200 ps.

In some embodiments, the light source may comprise an electronic triggering.

Alternatively, no delay unit may be included in the system 100 according to the invention. Delay unit 108 may be utilized according to the system of the present invention, by using a suitable geometry, in which a distance between the relevant components of the system produces an optical delay.

Streak camera 106 may utilize a streak tube. Streak camera 106 may comprise a photocathode for producing emission of electrons in proportion to intensity of the incident light, preferably, in the UV-VIS-NIR range, more preferably in the VIS-NIR. Streak camera 106 may be utilized for forming a streak image of light received at a desired time window corresponding to the time during which the streak image is formed. A streak camera image may be collected for each irradiation wavelength, each image having two dimensions time and distance along a line corresponding to a different locations. In addition, the laser power at each wavelength is also recorded.

Capturing a reflection (and/or other respective light input) of at least a portion of the plurality of light pulses, optionally, at a predefined time, corresponds to light traveling from the light source to the germinal disk and to the detector, which in turn, corresponds to a spatial resolution between about 0.1 mm and about 20 mm, preferably between about 1 mm and about 10 mm around the germinal disk.

In addition to recording streak camera images for each wavelength, the light source power at each wavelength may also be recorded and analyzed. Each image may be corrected to determine the differences in the laser power, using a mathematical transformation (e.g., normalization), which may provide 3D-hyperspectral data (time-distance-wavelength). As such, light captured from the germinal disk and optionally its surroundings may be analyzed 209 to determine at least one spectrum.

In some embodiments of the invention, analyzing the spectrum of an egg is obtained 209 in conjunction with a reference spectrum for correcting certain effects and/or conditions known in the art relating to components of the system, for example, non-linearity in the detector. In some embodiments, reference spectrum is obtained by further including measurement of background and/or reference spectra. In some embodiments, reference spectrum is obtained by calculation from a suitable model.

The spectra may be classified 210 using chemometric tools for identifying an egg state (e.g., whether or not it is fertile, and/or, for a fertile egg, its gender). For example, the ratio of the signals from the germinal disk at different irradiation wavelengths is used for determining the gender. In other embodiments, a series of signals originating from the germinal disk are recorded and the gender and/or the fertility is determined based on multivariate analysis. For example, principal component regression (PCR), principal component analysis (PCS), partial lease squares (PLS) and neural network based algorithms. In some embodiments, signals obtained from the germinal disk may undergo a mathematical manipulation prior to their utilization in chemometric calibration and analysis, for example, derivative, background correction, peak ratios, combination of peak ratios and signal normalization.

Computer 109 may be preferably also coupled to light source 102 for controlling the spectral region of interest, which provides intensity vs. location and time for each tested wavelength.

Figure 3:
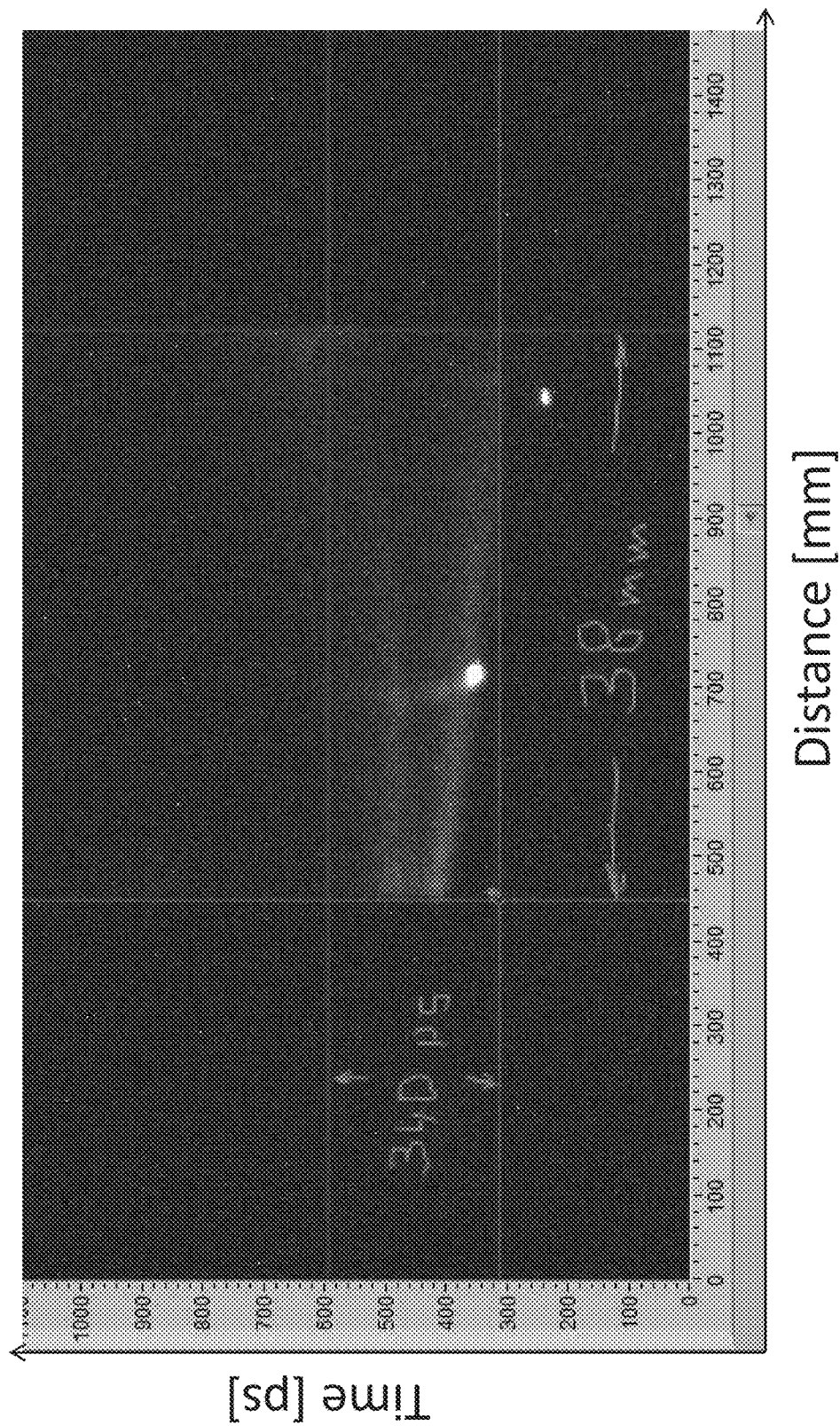
FIG. 3 is an image of intensity profiles of a reflected laser beam track passing through a 38 mm tube sample filled with diffusing material at a wavelength of 500 nm, as a function of time at picosecond resolution; according to some embodiments of the present invention.

Reference is now made to FIG. 3 demonstrating a measurement of a reflected laser beam track according to some embodiments of the method of the present invention. The measurement was conducted by using reflectance and fluorescence modes, in which an intensity profile of a reflected laser beam track impinging on a portion of a sample resembling an egg was observed. The angle between the laser beam and the detector was 90°. A 38 mm tube sample filled with diffusing material was used as a sample in the experiment, having substantially similar spectroscopic properties to an avian egg. Spectrum was obtained by passing through a 38 mm tube sample filled with diffusing material is an image of an intensity profile of a reflected laser beam track passing through a 38 mm tube sample filled with diffusing material at a wavelength of 500 nm.

The picosecond tunable laser used was Ekspla p12251B-10, a diode pumped laser with DPSS regenerative amp, 80 mj@ 1064 nm, 10 Hz, flash lamp pumped power amplifier, p20 option, harmonic modules, pretrig option for streak camera triggering and ps parametric generator.

The picosecond detector used was AXIS-PVI Ultrafast NIR Streak Camera System, by AXIS PHOTONIQUE INC. It was equipped with ultra-fast and regular sweep units, VS14 electromechanical shutter, effective cathode size 18 mm×75 μm, spectral response between 200 nm and 1300 nm, spatial resolution—25 lp/mm on the whole 18 mm, single-shot time resolution of 2, 4, 10, 20, 40, 100, 200 ps.

The germinal disk may also emit fluorescence when irradiated in the UV, thus such fluorescence may be utilized for determining fertilization and gender of the egg and/or assist in the determination. Fluorescence may be identified as lines of a steep slope in the distance-time figure (as depicted in FIG. 3), resulting from time dependence of the fluorescence emission at a given location in the egg.

An experimental cell having a 38 mm tube filled with a semi-transparent diffusing media was used as a model for egg protein 120. The experimental cell included a scatter layer as a model of egg shell 122; and a target as a model of germinal disk 124, as displayed in the illustration depicted in FIG. 5. The target mimicking the germinal disk was a droplet of Crimson red shade liquid PH, (used herein as artificial blood in spectroscopy). The laser beam 102 propagates from right to left. The x coordinate is the distance and the y coordinate is time. The beam propagates in the medium and the scattered light is observed. The light reaches the opposite edge of the tube and is reflected back. The intensity decreases with distance (and time). In this figure one reflection of the beam is observed, but several such reflections may also be observed. The white spot is due to the target, which reflects more light. Chemical information on the object may be obtained by measuring such images at various laser wavelengths. Both reflectance and absorbance modes are possible. The temporal resolution allows for ignoring strong signals originating from surfaces and/or other areas, such as egg shell, and isolating the signals from a specific location in the medium. As such, the SNR ratio is improved.

According to this exemplary embodiment, the distance between the light source 102 to the sample may be about 20 cm and the distance from the egg sample to the detector 106 may be about the same.

Figure 4B:
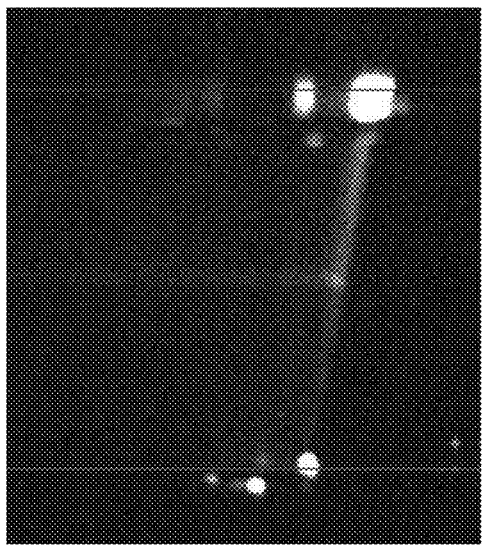
FIGS. 4A-4C are images of intensity profiles of a reflected laser beam track passing through an egg model at wavelengths of: (3A) $\lambda$=420 nm, (3B) $\lambda$=540 nm, and (3C) $\lambda$=620 nm as a function of time at picosecond resolution; according to some embodiments of the present invention.
Figure 4C:
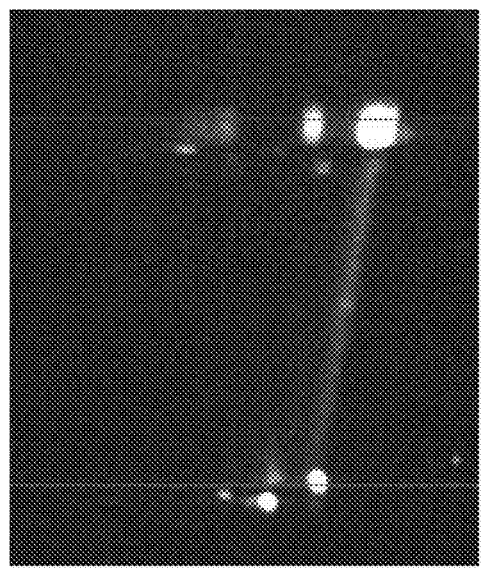
Figure 4A:
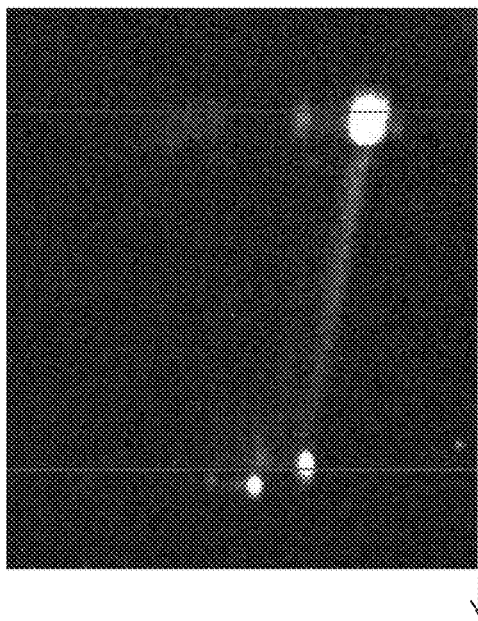
Figure 5:
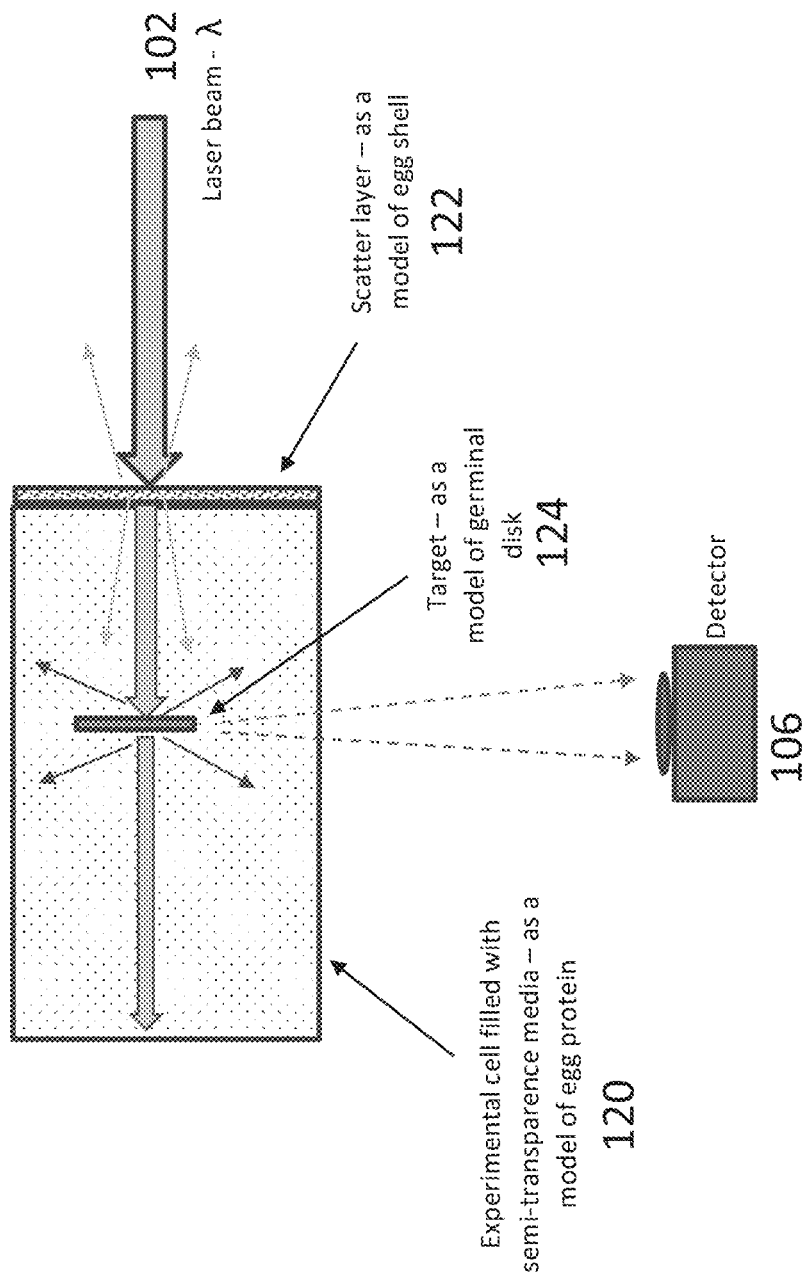
FIG. 5 is a schematic illustration of a system for spectral analysis according to FIGS. 4A-4C of the present invention.

The sample was a chamber of the size of an egg, filled with a scattering media (such as agar-agar) that mimics the egg's proteins as shown in FIG. 5, which is a schematic illustration of a system for spectral analysis according to FIGS. 4A-4C of the present invention.

The laser light pulses entered the chamber and the line-imaging was recorded using the streak camera as a function of time, at 90° configuration.

In additional examples provided in accordance with some embodiments of the present invention, a reflected laser beam track passing through an egg model at three different wavelengths of: $\lambda=420$ nm, $\lambda=540$ nm, and $\lambda=620$ nm was tested and the images of the intensity profiles thereof are shown in the FIGS. 4A-4C. FIG. 5 shows a schematic illustration of a system for spectral analysis according to FIGS. 4A-4C. A laser beam impinges on each of the sample and as a result, light is emitted. There is a relatively long fluorescence, in which the light intensity decreases as a function of time. This is represented by the essentially vertical white line in FIG. 4B, starting from the target point towards longer times (the vertical coordinate). The differences between the figures obtained at the three irradiation wavelengths: The differences in the decay of the white line represents differences in the absorption/scattering of the medium and of the target at the different wavelengths. As appreciated, only one wavelength (540 nm) indices significant fluorescence, indicating that the spectral excitation and emission characteristics of the target can be measured by such a setup.

In another of its aspects, the invention provides a method for screening a plurality of eggs, the method comprising: illuminating a plurality of eggs with a plurality of light pulses, each one of said plurality of light pulses having: a wavelength between about 400 nanometer (nm) and about 1500 nm, a width between about 0.5 picoseconds (ps) and about 500 ps, and an intensity between about 0.1 milliJoule (mJ) and about 100 mJ; capturing a plurality of reflections of at least a portion of the plurality of light pulses at a time delay corresponding to light reflected from each one of said plurality of eggs in an interval of between about 1 mm and about 20 mm; analyzing each one of the captured reflections to determine at least one spectrum of each of said plurality of light pulses; and classifying at least one of a gender and a fertility state of each one of said plurality of eggs according to said at least one spectrum.

The method disclosed herein, further comprising discarding an egg from said plurality of eggs for which said at least one of a gender and a fertility state does not meet a predetermined state.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately and/or in any suitable subcombination and/or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method and/or structure may include additional ingredients, steps and/or parts, but only if the additional ingredients, steps and/or parts do not materially alter the basic and novel characteristics of the claimed composition, method and/or structure.

As used herein, the singular form "a", "an" and "the" include plural references unless the context clearly dictates otherwise. For example, the term "a compound" and/or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional and/or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately and/or in any suitable subcombination and/or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent and/or patent application was specifically and individually indicated to be incorporated herein by reference. In addition, citation and/or identification of any reference in this application shall not be construed as an admission that such reference is available as prior art to the present invention. To the extent that section headings are used, they should not be construed as necessarily limiting.

What is claimed is:

1. A method for detecting a state of an egg, the method comprising:
   illuminating an egg with a plurality of light pulses, each one of said plurality of light pulses having:
      a wavelength between about 400 nanometer (nm) and about 1500 nm,
      a width between about 0.5 picoseconds (ps) and about 500 ps, and
      an intensity between about 0.1 milliJoule (mJ) and about 100 mJ;
   capturing a reflection of at least a portion of the plurality of light pulses at a time delay corresponding to light reflected from within said egg in an interval of between about 1 mm and about 20 mm;
   analyzing the captured reflection to determine at least one spectrum of each of said plurality of light pulses; and
   classifying at least one of a gender and a fertility state of said egg according to said at least one spectrum.

2. The method according to claim 1, wherein each of at least some of said plurality of light pulses has an intensity of between about 0.2 and about 10 mJ per pulse.

3. The method according to claim 1, further comprising configuring each of at least some of said plurality of light pulses to comprise light at a first wavelength of between about 300 nm and about 750 nm and light at second wavelength of between about 900 nm and about 1400 nm.

4. The method according to claim 3, wherein the first wavelength is between about 500 nm and about 700 nm and the second wavelength is between about 950 nm and about 1350 nm.

5. The method according to claim 1, wherein each of at least some of the plurality of light pulses having a beam area of between about 0.5 and about 5 mm².

6. The method according to claim 1, wherein the capturing a reflection of plurality of light pulses is by directing the reflected light pulses into a streak camera.

7. The method according to claim 1, further comprising discarding the egg for which said condition does not match a predetermined condition.

8. The method according to claim 1, wherein said classifying is carried out up to 3 days after incubation of the egg.

9. The method according to claim 1, wherein said at least one spectrum is selected from a group consisting of: a reflectance spectrum, a transmittance spectrum, a fluorescence spectrum and a derivative spectrum.

10. The method according to claim 9, wherein said at least one of the spectrum is obtained by analyzing a portion of captured light emanated from said egg at an angle below about 180° relative to a longitudinal axis of the egg.

11. The method according to claim 1, wherein said time delay is set from time of illuminating said egg with a plurality of light pulses.

12. A method for detecting a state of an egg, the method comprising:
   illuminating an egg with a plurality of light pulses, each one of said plurality of light pulses having:
   a wavelength between about 400 nanometer (nm) and about 1500 nm,
   a width between about 0.5 picoseconds (ps) and about 500 ps, and
   an intensity between about 0.1 milliJoule (mJ) and about 100 mJ;
   capturing a reflection of at least a portion of the plurality of light pulses at a temporal resolution of between about 0.5 ps and about 500 ps;
   analyzing the captured reflection to determine at least one spectrum of each of said plurality of light pulses; and
   classifying at least one of a gender and a fertility state of said egg according to said at least one spectrum.

13. A system for detecting a condition of an egg, the system comprising:
   a light source for illuminating the egg with a plurality of light pulses, each one of said plurality of light pulses having:
   a wavelength between about 400 nanometer (nm) and about 1500 nm,
   a width between about 0.5 picoseconds (ps) and about 500 ps, and
   an intensity between about 0.1 milliJoule (mJ) and about 100 mJ;
   a detector for capturing a reflection of at least a portion of the plurality of light pulses at a time delay corresponding to light reflected from within said egg in an interval of between about 1 mm and about 20 mm;
   a processor for analyzing the captured reflection to determine at least one spectrum of each of said plurality of light pulses so as to classify at least one of a gender and a fertility state of said egg according to said at least one spectrum.

14. The system according to claim 13, wherein the detector comprises a streak camera.

15. The system according to claim 13, wherein the detector having a resolution between about 1 ps and about 300 ps.

16. The system according to claim 13, wherein the light source comprises at least one laser.

17. The system according to claim 16, wherein the laser is a diode pumped laser.

18. The system according to claim 13, wherein the laser is a Nd:YAG laser.

19. The system according to claim 13, wherein the laser is a wavelength tuneable laser.

20. The system according to claim 13, comprising a trigger jitter having a resolution below 200 ps.

* * * * *